United States Patent [19]

Kindlmann

[11] Patent Number: 4,911,817

[45] Date of Patent: Mar. 27, 1990

[54] ELECTROPHORESIS APPARATUS

[75] Inventor: Peter J. Kindlmann, Guilford, Conn.

[73] Assignee: Eastman Kodak Company, Rochester, N.Y.

[21] Appl. No.: 260,150

[22] Filed: Oct. 20, 1988

[51] Int. Cl.⁴ .............................................. B01D 13/02
[52] U.S. Cl. ............................ 204/299 R; 204/300 R; 204/182.8
[58] Field of Search ............. 204/182.8, 299 R, 300 R

[56] References Cited

U.S. PATENT DOCUMENTS

| | | | |
|---|---|---|---|
| 4,473,452 | 9/1984 | Cantor et al. | 204/299 R |
| 4,569,741 | 2/1986 | Pohl | 204/299 R |
| 4,661,451 | 4/1987 | Hansen | 204/299 R |
| 4,737,251 | 4/1988 | Carle et al. | |
| 4,740,283 | 4/1988 | Laas et al. | 204/182.8 |

OTHER PUBLICATIONS

Biotechnology, Dec. 1986, p. 1054, "Tricks Tame Megabase DNA Fragments", Douglas McCormick.
Science, vol. 234, Dec. 19, 1986, pp. 1582–1585, "Separation of Large DNA Molecules . . . Fields", Gilbert Chu et al.
Nucleic Acids Research, vol. 16, No. 15, Aug. 11, 1988, pp. 7563–7582, "Optimized Conditions". . . of DNA, Bruce W. Birren et al.

*Primary Examiner*—John F. Niebling
*Assistant Examiner*—David G. Ryser
*Attorney, Agent, or Firm*—Dana M. Schmidt

[57] ABSTRACT

In an apparatus for electrophoresis, using a support for a gel and a liquid buffer, a plurality of driving electrodes arrayed in spaced relation to one another so as to contact the medium, and a plurality of sensing electrodes arrayed in spaced relation to one another and the driving electrodes so as to contact the medium. Each sensing electrode is preferably radially inward of and paired with a single one of the driving electrodes. Means are provided respectively for providing electrical potentials to be applied to selected ones of the driving electrodes, for applying the provided potentials, for sensing electrical potentials at selected ones of the sensing electrodes, and for adjusting the applied potentials to maintain the sensed potential at a selected value at a sensing electrode of each pair. The apparatus may be programmably controllable so as to enable an electric field to be modulated in amplitude and direction, as a function of time.

11 Claims, 2 Drawing Sheets

ELECTROPHORESIS APPARATUS

FIELD OF THE INVENTION

This invention pertains to electrophoresis. More specifically, this invention pertains to improvements in electrophoresis apparatus whereby an electrical field can be directionally modulated, so as to tend to cause a molecule being electrophoresed to migrate in any desired direction.

BACKGROUND OF THE INVENTION

It has been known heretofore that electrical parameters governing gel electrophoresis, i.e., electrophoresis on a flat surface of a gel, in a buffer solution, include the magnitude of the electric field, the direction of the electric field, and the evolution of the magnitude and direction of the electric field as functions of time, as well as the type and temperature of the buffer solution, the material and configuration of the electrodes, and other factors. Both homogeneous and nonhomogeneous electric fields have been used in gel electrophoresis. An electric field is regarded as homogeneous if it is uniform, in magnitude and direction, across the flat surface of the gel at any moment in time.

It also has been known heretofore that pulsed modulation of the magnitude of the electric field, in its direction, or both, enhances the utility of gel electrophoresis, particularly in the separation of proteins, nucleic acids, and other such macromolecules. Pulsed modulation refers to modulation at timed intervals, between which the electric field may be substantially uniform across the flat surface of the gel.

In recent years, apparatus for gel electrophoresis have advanced from apparatus employing two parallel driving electrodes, or two parallel arrays of driving electrodes, which apply electric fields tending to cause molecules to migrate along straight lines between such electrodes, to apparatus employing polygonal arrays of driving electrodes, which apply electric fields that can be directionally modulated so as to tend to cause molecules to migrate along non-straight paths, e.g., paths having corners or zig-zag paths.

In one heretofore known type of apparatus for gel electrophoresis, as mentioned above, a square array of driving electrodes is provided, which enables electric fields to be alternatively applied in transverse directions so as to tend to cause samples being electrophoresed to migrate in paths that change direction at 90° angles. See, e.g., Cantor et al. U.S. Pat. No. 4,473,452, which discloses that such fields can be substantially uniform, if applied by and between paired electrodes in like numbers on opposite sides of the square array, or substantially fan-shaped, if applied by and between one electrode on one end of a given side of the square array and plural electrodes on the opposite side of the square array. This patent also mentions that each electrode can be selectively maintained at any positive or negative electrical potential within a selected range.

In another heretofore known type of apparatus for gel electrophoresis, as mentioned above, a hexagonal array of driving electrodes is provided, which enables homogeneous electrical fields to be alternatingly applied at timed intervals so as to cause molecules being electrophoresed to migrate in zig-zag paths. See, e.g., Biotechnology, December 1986, page 1054, which refers to electrophoresis in such apparatus as contour-clamped homogeneous electric field (CHEF) electrophoresis, and which compares CHEF electrophoresis to other heretofore known techniques including pulsed-field gel electrophoresis (PFGE) and field-inversion electrophoresis. See, also, Chu et al., "Separation of Large DNA Molecules by Contour-Clamped Homogenous Electric Fields," Science, Dec. 19, 1986, Vol. 234, pp. 1582–5. An apparatus employing parallel driving electrodes, for field-inversion electrophoresis, is disclosed in Carle et al. U.S. Pat. No. 4,737,251.

Although some of the heretofore known apparatus and techniques discussed in the preceding paragraphs have been valuable contributions to the art of electrophoresis, there has remained a need, to which this invention is addressed, for greater flexibility in directional modulation of an electric field in an apparatus for electrophoresis.

SUMMARY OF THE INVENTION

This invention provides an apparatus for conducting electrophoresis in a gel, which is immersed in a buffer solution, or for conducting electrophoresis in another suitable medium, which has an array of driving electrodes and an array of sensing electrodes, each in contact with the medium.

The driving electrodes are arrayed in spaced relation to one another, preferably along a closed, curved path. The sensing electrodes are distinct from the driving electrodes and also are arrayed in spaced relation to one another, preferably also along a closed, curved path spaced from, and lying on the concave side of, the path of the driving electrodes.

Preferably, the driving and sensing electrodes are arrayed respectively along concentric circles, with the circle along which the driving electrodes are arrayed enclosing the circle along which the sensing electrodes are arrayed. Preferably, the driving and sensing electrodes are arrayed in equal numbers in electrode pairs, and fixed in place, in which each sensing electrode is radially inward of and paired with a single one of the driving electrodes. As a highly preferred example, twenty-four driving electrodes and twenty-four sensing electrodes may be so arrayed, the driving electrodes in equally spaced intervals along a circle and the sensing electrodes in like intervals along a circle having a lesser radius.

Means are provided respectively for providing electrical potentials to be applied to selected ones of the driving electrodes, for applying such potentials, for sensing electrical potentials at selected ones of the sensing electrodes, and for adjusting the applied potentials to maintain the sensed potentials at selected values. If the driving and sensing electrodes are arrayed in equal numbers in electrode pairs, as discussed above, the adjusting means adjusts the applied potentials to maintain the sensed potential at a selected value at the sensing electrode of each electrode pair.

Since each electrode pair may be independently controlled, the apparatus may be programmably controllable, as for example by means of a microprocessor, to enable an electric field to be directionally modulated, in any direction, e.g., as a function of time.

These and other objects, features, and advantages of this invention are evident from the following description of a preferred embodiment of this invention with reference to the accompanying drawing.

DETAILED DESCRIPTION OF PREFERRED EMBODIMENT

Figure 1:
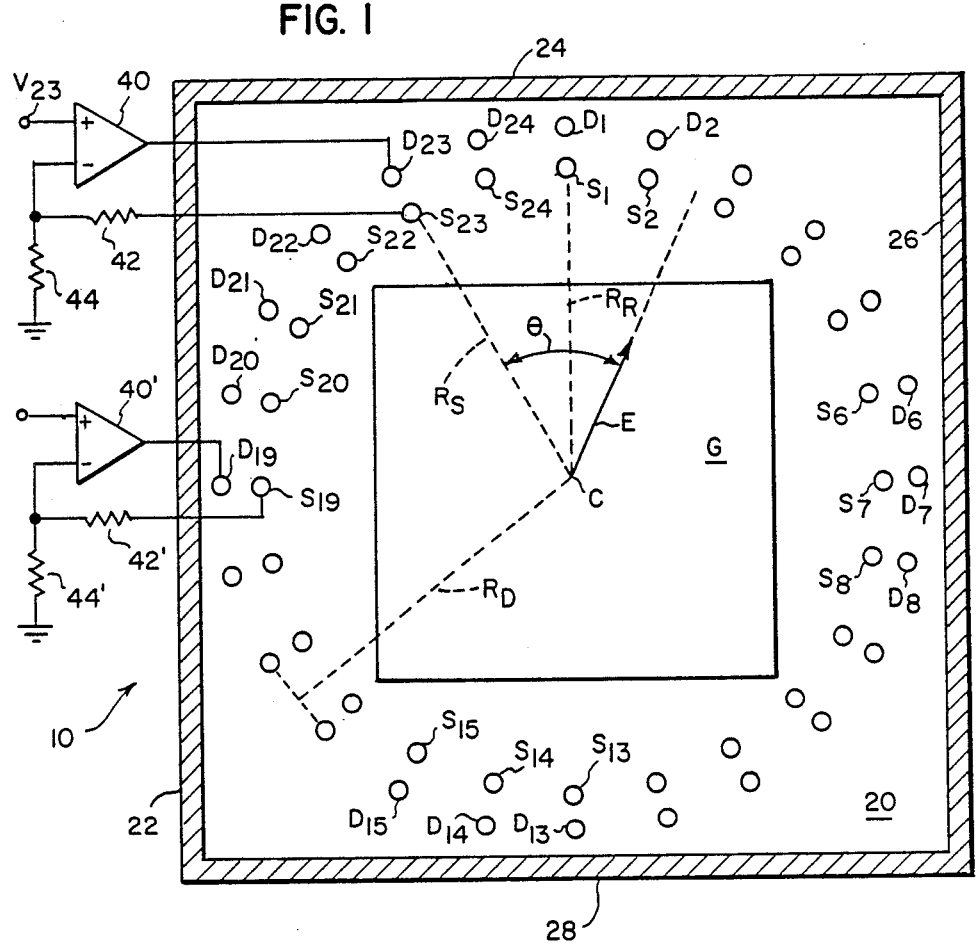
FIG. 1 is a semi-diagrammatic view, partially in section, of a support for an electrophoresis gel, a circular array of driving electrodes, a circular array of sensing electrodes, and an exemplary portion of electrical circuitry associated with the driving and sensing electrodes, in an electrophoresis apparatus constituting a preferred embodiment of this invention.

As represented in the drawing, an apparatus 10 for electrophoresis employing a gel matrix G, in a buffer solution, constitutes a preferred embodiment of this invention.

Such a gel matrix and such a buffer solution are conventional in gel electrophoresis. In the preferred embodiment, the gel matrix G may be an aqueous gel of 1% agarose occupying a square area, which measures about 20 cm × 20 cm. Any conventional buffer solution compatible with the gel matrix G may be used. The buffer solution must have sufficient resistivity to avoid short-circuits between driving electrodes described below. Two preferred formulations for buffer solutions are set forth below in Tables A and B respectively. Preferably these are used in 0.5X strengths.

TABLE A

TAE (1X formulation)
0.04 Molar Tris-acetate [Tris(hydroxymethyl)aminomethane actetate]
0.001 Molar EDTA [ethylenediamenetetraacetic acid]
balance, water
pH = 8.0 approximately

TABLE B

TBE (10X formulation)
0.89 Molar Tris Base [Tris(hydroxymethyl)aminomethane]
0.89 Molar Boric Acid [$H_3BO_3$]
0.02 Molar EDTA [ethylenediamenetetraacetic acid]
balance, water
pH = 8.3 approximately The apparatus 10 comprises an electrophoresis chamber of a conventional type including a rectangular, horizontal support 20 for the gel matrix G and the buffer solution and including outer walls 22, 24, 26, 28, which contain the buffer solution. The horizontal support 20 and the outer walls are made of a non-electrically conducting material, e.g., glass or plexiglass.

In order to maintain the homogeneity of the electric field, the depth and temperature uniformity of the buffer solution should be controlled, and the gel matrix G should be immersed entirely within a uniform layer of the buffer solution, not recessed into a well. For example, it is believed that a 1% depth variation leads to a localized 1% error in the magnitude of the electric field; the direction of the electric field is also affected, but in a more complex way, which is believed to depend upon the depth variation gradients. The buffer solution should be cooled, in order to maintain a uniform temperature, by recirculating through cooling means (not shown) conventional in electrophoresis. Precise temperature control is important because the conductivity of a buffer solution can vary by as much as 3% per degree C. variation.

Preferably, the support 20 is levelled, and the buffer solution covers the gel matrix G at a depth of about 1 cm and is maintained at a uniform temperature of 5° to 15° C. Maintaining the buffer solution at such a temperature also suppresses denaturing of the gel matrix G and of the sample.

The apparatus 10 comprises twenty-four driving electrodes $D_n$ (wherein n represents integers from 1 to 24 inclusive) in a circular array having a radius $R_D$ and twenty-four sensing electrodes $S_n$ (wherein n again represents integers from 1 to 24 inclusive) in a circular array having a radius $R_s$ and being disposed fixedly and concentrically within the circular array of driving electrodes. Each of the driving and sensing electrodes is preferably mounted to make optimal electrical contact with the liquid buffer in the electroporesis chamber of the apparatus 10, by penetrating the buffer solution vertically over its full depth. Each of the driving electrodes may be advantageously made of a platinum foil covering a cylindrical core, or of coiled or folded lengths of platinum wire longer than the depth of the buffer solution, or of a porous conductive ceramic, e.g., a porous titanium suboxide available commercially from Ebonex Technologies, Inc. under the "Ebonex" trademark. Each of the sensing electrodes may be advantageously made of a platinum wire or other conducting media. In the preferred embodiment, the circular array of the sensing electrodes has a radius $R_s$ of about 16.5 cm, the circular array of driving electrodes has a radius $R_D$ of about 18 cm, and the geometric center of the 20 cm × 20 cm square occupied by the gel matrix G coincides with the common center of the circular arrays. A reference radius $R_R$ is indicated on FIG. 1 for a purpose to be later mentioned. The driving electrodes are arrayed in equally spaced relation to one another, i.e., at 15° intervals. The sensing electrodes are arrayed similarly, at like intervals, so that each of the sensing electrodes is positioned radially inward of one of the driving electrodes. Thus, the driving electrode $D_1$ and the sensing electrodes $S_1$ are located on a common radius, i.e., the reference radius $R_R$ the driving electrode $D_2$ and the sensing electrode $S_2$ are located on a common radius, and so on. The driving and sensing electrodes are arrayed, on the common radii, in electrode pairs. Thus, the driving electrode $D_1$ and the sensing electrode $S_1$ constitute a first electrode pair, the driving electrode $D_2$ and the sensing electrode $S_2$ constitute a second electrode pair, and so on.

Since the electrophoresis chamber of the apparatus 10 contains a bounded, uniformly electrically conducting layer of the buffer solution, the potential distribution necessary for a homogeneous field within the boundary of such layer is the same as would exist if such layer were embedded in a much larger region exhibiting a homogeneous field. Field conditions within a region isolated as if removed from a larger whole can be maintained if boundary conditions of the region can be matched. The apparatus 10 enables the boundary conditions of the circular array of sensing electrodes to be matched as if the circular array of sensing electrodes were within a much larger region exhibiting a uniform field.

At each electrode pair constituted by a driving electrode and a sensing electrode, an electrical potential is applied directly to the driving electrode, e.g., between the driving electrode and a point of common potential usually referred to as ground, of a suitable magnitude to cause an electrical potential of a desired magnitude to occur at the sensing electrode of such electrode pair. Moreover, the electrical potential is sensed at the sensing electrode of such pair. The potential required at each sensing electrode varies depending on the desired field. In turn, the potential at the corresponding driving electrode differs from that of its sensing electrode by varying amounts, as determined by parameters such as buffer solution formulation, electrical current, electrode polarity, and spacing.

To establish a uniform field of a desired amplitude E, e.g., between 2 volts per cm and 10 volts per cm, in a desired direction from the center of the circular arrays, as shown by an arrow representing a vector in FIG. 1, the required voltage at any given one of the sensing electrodes is given by the equation:

$$V_s = ER_s \cos \theta$$

where E is the desired amplitude, as mentioned above, $R_S$ is the radius of the circular array of sensing electrodes, and $\theta$ is the angle between a radius through the given one of the sensing electrodes and a radius coinciding with the vector arrow, as shown in FIG. 1. The electrical potential at a central region C of the gel matrix G may be arbitrarily held at zero potential, and, therefore, the central region C of the gel matrix G may be said to be grounded. Typically, for an electrical field of a magnitude between 2 volts per cm and 10 volts per cm, voltages of up to $\pm 165$ V are sensed at the sensing electrodes. Typically, the electrical potentials applied at the driving electrodes are up to 25 V greater, more commonly up to 15 V greater, than the electrical potentials sensed at the sensing electrodes. Since the direction of the electric field can be quite arbitrary, it is not necessary to align the direction of the electric field with the angular position of any electrode or electrode pair of the circular arrays.

As a representative example, for an electrical field having a magnitude of 5 V per cm and being directed at an angle of 25° clockwise (as shown) from the reference radius $R_R$, the required voltages at the sensing electrodes are given below in Table C, wherein the number in the column at the extreme left is the subscript of the designation of the sensing electrode, and wherein all data are approximate.

TABLE C

| Electrode | Θ* | cosθ | Vs(=ER$_s$cosθ) |
|---|---|---|---|
| 1 | 335° | 0.906 | 74.7 V |
| 2 | 350° | 0.985 | 81.3 V |
| 3 | 5° | 0.996 | 82.2 V |
| 4 | 20° | 0.940 | 77.5 V |
| 5 | 35° | 0.819 | 67.6 V |
| 6 | 50° | 0.643 | 53.0 V |
| 7 | 65° | 0.423 | 34.9 V |
| 8 | 80° | 0.174 | 14.3 V |
| 9 | 95° | −0.087 | −7.2 V |
| 10 | 110° | −0.342 | −28.2 V |
| 11 | 125° | −0.574 | −47.3 V |
| 12 | 140° | −0.766 | −63.2 V |
| 13 | 155° | −0.906 | −74.8 V |
| 14 | 170° | −0.985 | −82.2 V |
| 15 | 185° | −0.996 | −82.2 V |
| 16 | 200° | −0.940 | −77.5 V |
| 17 | 215° | −0.819 | −67.6 V |
| 18 | 230° | −0.643 | −53.0 V |
| 19 | 245° | −0.423 | −34.9 V |
| 20 | 260° | −0.714 | −14.3 V |

TABLE C-continued

| Electrode | Θ* | cosθ | Vs(=ER$_s$cosθ) |
|---|---|---|---|
| 21 | 275° | 0.087 | 7.2 V |
| 22 | 290° | 0.342 | 28.2 V |
| 23 | 305° | 0.574 | 47.3 V |
| 24 | 320° | 0.766 | 63.2 V |

*Measurements are made clockwise from vector E.

A constant positive or negative voltage may be arbitrarily added to all voltages given in Table C above. The corresponding absolute values of the electrical potentials applied to the driving electrodes exceed the absolute values of the electrical potentials sensed at the sensing electrodes in the respective electrode pairs, typically by up to 25 V, more commonly up to 15 V, but depend in complex ways on such factors as the composition of the buffer solution, the polarities, currents drawn by the respective electrodes, and surface areas of the respective electrodes.

Advantageously, the feedback approach taken by this invention allows such factors as are mentioned in the preceding paragraph to be largely ignored. Prudence still dictates, however, that driving electrodes having larger surface areas are preferred over thin wires. Larger surface areas diminish the potential drops in the immediate vicinity of the driving electrodes and lessen the density of gas bubbles formed by electrolysis, thus reducing excess power dissipation outside the electrophoresis region. Reduced power loss minimizes the cooling requirements. For example, driving electrodes with an exposed surface area of about 0.25 cm$^2$ are preferred.

Herein, all references to a driving electrode are intended to refer to an electrode which, at a given potential applied thereto, provides or receives an electromotive force tending to cause molecules to migrate toward or away from an electrode of a different potential, e.g., zero potential or a potential of an opposite polarity. For example, if it were grounded, the center C of the gel matrix G would define a ground potential of zero value vis-a-vis each of the driving electrodes to which electrical potentials are applied. Irrespective of whether the center C of the gel matrix G is at ground potential, electrical potentials can be thus applied to a selected two or more, and as many as all of the driving electrodes, to establish an electric field in any arbitrary direction. Therefore, herein, all references to selected ones of the driving electrodes are intended to refer to as few as two of the driving electrodes, and to as many as all of the driving electrodes. Similarly, herein, all references to selected ones of the sensing electrodes are intended to refer to as few as two of the sensing electrodes and as many as all of the sensing electrodes.

A high gain, error-sensing, differential amplifier arranged for negative feedback is provided for each of the twenty-four electrode pairs. As representative examples shown in FIG. 1, such an amplifier 40 is shown, as provided for the electrode pair constituted by the driving electrode $D_{23}$ and the sensing electrode $S_{23}$, and another such amplifier 40' is shown, as provided for the electrode pair constituted by the driving electrode $D_{19}$ and the sensing electrode $S_{19}$. Each amplifier comprises a high gain, integrated circuit operational amplifier with a discrete component output stage employing conventional high voltage MOS transistors, to deliver output voltages of up to $\pm 250$ V, and capable of switching speeds on the order of 100 μsec. The output stage of each amplifier is connected directly to the driving electrode of the electrode pair for which such amplifier is provided. As a representative example shown in FIG. 1, the output stage of the amplifier 40 is connected directly to the driving electrode $D_{23}$.

Each amplifier compares an electrical potential corresponding to the electrical potential sensed at the sensing electrode of the electrode pair for which such amplifier is provided, to a program voltage supplied to such amplifier for such electrode pair in a manner to be later described. The electrical potential sensed at the sensing electrode of such electrode pair may be and, as shown, is scaled down by a factor of 100, before being fed back to such amplifier, by a voltage divider comprising a resistor connected to the sensing electrode of such electrode pair and a resistor connected between the resistor and ground. As a representative example shown in FIG. 1, a voltage divider scaling down the electrical potential sensed at the sensing electrode $S_{23}$ comprises a resistor 42 having a resistance of 1 Meg ohms connected to the sensing electrode $S_{23}$ and a resistor 44 having a resistance of 10k ohms connected between the resistor 42 and ground. Such resistor values produce negligible current flow through the sensing electrodes and allow them to sense the buffer solution potential at their locations without errors due to electrochemical electrode activity. Similarly, as shown, a voltage divider scaling down the electrical potential sensed at the sensing electrode $S_{19}$ comprises a resistor $42'$ connected to the sensing electrode $S_{19}$ and a resistor $44'$. Each amplifier applies an electrical potential having a value equal to a program voltage plus or minus a feedback voltage, which is provided by such amplifier in response to the scaled down, sensed voltage fed back to such amplifier, the applied potential being applied to the driving electrode of the electrode pair for which such amplifier is provided. Consequently, an electrical potential of the desired magnitude tends to occur at the sensing electrode of such electrode pair.

Figure 2:
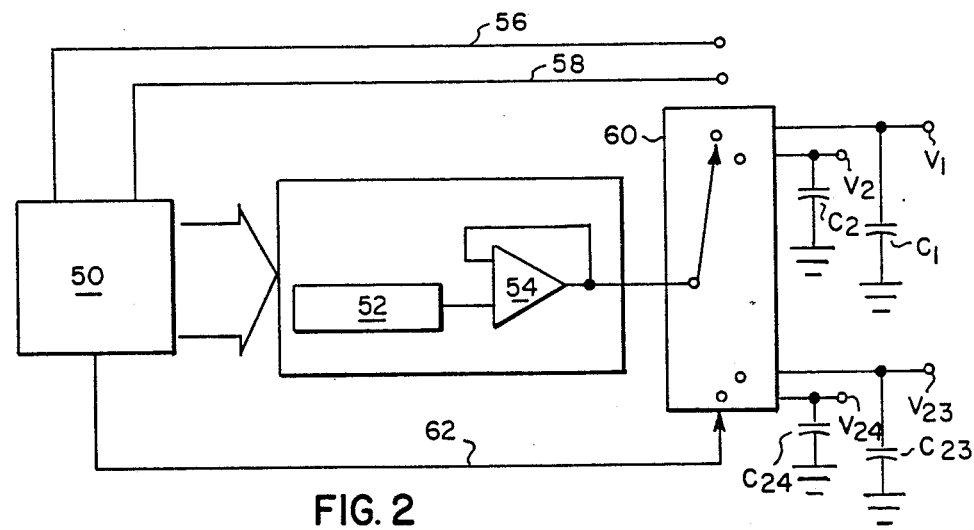
FIG. 2 is a block diagram of other portions of electrical circuitry of the electrophoresis apparatus of FIG. 1.

As shown in FIG. 2, the program voltage for each electrode pair is provided, as a digital signal, from a data source 50, which generates or retrieves such program voltage. Further, the data source 50 supplies the digital signal through a digital-to-analog converter 52, which converts the digital signal to an analog voltage, through a buffer 54, which buffers the analog voltage, and through a multiplexer 60, to the amplifier provided for such electrode pair. The multiplexer 60, which has a timed cycle that may be controlled by the data source 50 through a lead 62, or independently, has one input stage, which is connected to the digital-to-analog converter 52 through the buffer 54, and twenty-four output stages, one for each electrode pair. The output stage of the multiplexer 60 for each electrode pair includes an output terminal, which is connected to the amplifier for such electrode pair, and a capacitor for storing a voltage, i.e., the program voltage supplied by the multiplexer 60 to the amplifier for such electrode pair. Thus, as shown in FIG. 2, the multiplexer 60 has an output stage including such an output terminal $V_1$ and such a capacitor $C_1$ for the electrode pair constituted by the driving electrode $D_1$ and the sensing electrode $S_1$, and such an output terminal $V_2$ and such a capacitor $C_2$ for the electrode pair constituted by the driving electrode $D_2$ and the sensing electrode $S_2$. Also as shown in FIG. 2, the multiplexer 60 has such an output terminal $V_{23}$ and such a capacitor $C_{23}$ for the electrode pair constituted by the driving electrode $D_{23}$ and the sensing electrode $S_{23}$ and such an output terminal $V_{24}$ and such a capacitor $C_{24}$ for the electrode pair constituted by the driving electrode $D_{24}$ and the sensing electrode $S_{24}$. The output terminal $V_{23}$ is shown also in FIG. 1.

In place of the multiplexer 60, a plural number of multiplexers may be used, each addressing a different group of the electrode pairs, e.g., six multiplexers, each addressing a different group of four electrode pairs, whereupon, in place of the digital-to-analog converter 52 and the buffer 54, as a subcombination, a like number of subcombinations of digital-to-analog converters and buffers may be used, each subcombination comprising a digital-to-analog converter supplying an analog signal through a buffer, and each subcombination addressing a different one of the multiplexers. Although shown with a mechanical symbol, the multiplexer 60 preferably is electronic.

The data source 50 may be any suitable source of digital signals representing the programming voltages for the driving electrodes. Thus, the data source 50 may comprise a computer, microprocessor, or programmable controller, which generates such signals pursuant to a stored program. The stored program may reside in an erasable, programmable, read-only memory (EPROM) which is used as a "look up" table, and from which data are retrieved, as digital signals, pursuant to external control through external leads 56, 58, shown in FIG. 2. External control of such a memory may be provided by an array of switches. In a simpler form, the data source 50 may comprise a resistor-divider string, which is adapted to be selectively switched. Details of the data source 50 are outside the scope of this invention.

The amplifiers noted above and the voltage dividers associated therewith apply electrical potentials, as provided by the digital-to-analog converter 52 through the buffer 54 and the multiplexer 60, to selected ones of the driving electrodes. As the voltage dividers sense electrical potentials at selected ones of the sensing electrodes, the amplifiers adjust the applied potentials so as to tend to maintain the sensed potentials at selected values. The driving electrodes to which electrical potentials are applied and the sensing electrodes at which electrical potentials are sensed are selected from the same electrode pairs. Moreover, the capacitors noted above store the provided potentials, and the multiplexer 60 restores the potentials stored by such capacitors to the provided potentials periodically, e.g., every 200 to 600 microseconds.

By appropriate selection and timed control of the programming voltages to be thus applied to selected ones of the driving electrodes, the apparatus 10 may be readily adapted to practice a wide range of different techniques of gel electrophoresis, as exemplified by but not limited to such techniques as are discussed in the Cantor et al. and Carle et al. patents noted above and in the Biotechnology and Science references noted above.

A uniform field that is constant as a function of time can be thus used to separate smaller molecules of a sample. Forcing the molecules of a sample to change direction of movement at an angle, however, causes the smaller molecules to proceed faster than the larger molecules.

To practice gel electrophoresis according to a technique similar to the technique discussed in the Cantor et al. patent noted above, the electric field discussed in the above example as having a magnitude of 5 V per cm and as being directed at an angle of 25° (clockwise as shown) from the reference radius $R_R$ can be initially applied for a specified period of time, e.g., from 1 sec. to 120 sec., or more, whereupon the electric field can be angularly rotated 90° (i.e., new electrical potentials are applied to the driving electrodes so that the voltage sensed initially at the sensing electrode $S_1$, is sensed at the sensing electrode $S_7$, so that the voltage sensed initially at the sensing electrode $S_2$ is sensed at the sensing electrode $S_8$, and so on) and there applied for the same period of time, or for a different period of time, whereupon the electric field can be similarly rotated back (to where the electric field was applied initially) and there applied for the same period of time, or for a different period of time, and so on for a desired number of such alternations of the electric field.

To practice gel electrophoresis according to a technique similar to the technique disclosed in the Carle et al. patent noted above, the electric field discussed above as having a magnitude of 5 V per cm and as being directed at an angle of 25° (clockwise as shown) from the reference radius $R_R$ can be initially applied for a specified period of time, e.g., about 120 sec., whereupon the electric field can be angularly rotated 180° (i.e., new electrical potentials are applied so that the voltage sensed initially at the sensing electrode $S_1$, is sensed at the sensing electrode $\tilde{S}_{13}$, so that the voltage sensed initially at the sensing voltage $S_2$ is sensed at the sensing electrode $S_{14}$, and so on) and there applied at a selected, lower magnitude, e.g., 5/3 V per cm, for the same period of time, or 5 V per cm for a shorter (e.g., 40 sec.) period of time, whereupon the electric field can be similarly rotated back (to where the electric field was applied initially) and there applied at its original magnitude of 5 V per cm for the same period of time, and so on for a desired number of such alternations of the electric field.

To practice gel electrophoresis according to a technique similar to the technique discussed in the Biotechnology reference noted above, an electric field can be analogously switched back and forth 120°, at timed intervals.

The electric field also may be so controlled as to undergo many small step changes in amplitude and/or direction in a rapid sequence, so as to approximate a smooth evolution of angle and amplitude, over time. As will be apparent from the earlier discussion, any angle of electric field can be programmed, and within the ±250 Volt constraints of amplifiers 40, any amplitude between 0 and 10 V/cm can be programmed. The field can also be controlled to cause a funneling effect tending to narrow a band of molecules of a sample being electrophoresed as the band progresses along the gel matrix G.

Figure 3:
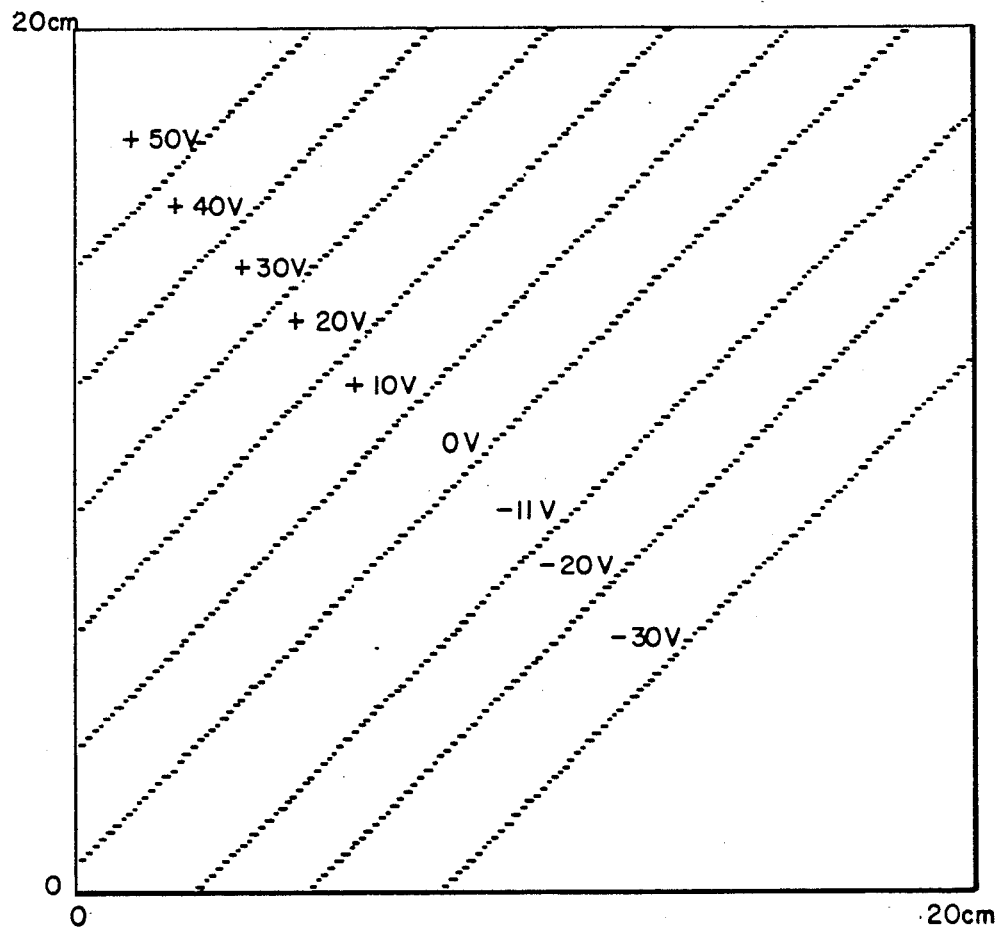
FIG. 3 is a plot of isopotential contours achieved using the apparatus of this invention.

FIG. 3 illustrates the kind of uniform field that can be generated in matrix G, as actually measured at isopotentials using the arrangement of FIG. 1. In this experiment, vector E was directed towards electrodes $D_{22}$ and $S_{22}$. The buffer was 1 cm deep (0.5X TBE formulation), at about 28° C., with a voltage gradient of about 5 V/cm and power dissipation in the buffer of about 60 W.

Various modifications may be made in the apparatus 10 without departing from the scope and spirit of this invention.

What is claimed is:

1. An apparatus for electrophoresis in a medium that includes a buffer solution comprising:
    (a) a plurality of driving electrodes arrayed in spaced relation to one another in contact with the medium;
    (b) a plurality of sensing electrodes arrayed in spaced relation to one another and to said driving electrodes in contact with the medium; and
    (c) providing means for providing electrical potentials to be applied to selected ones of the driving electrodes, means for applying the provided potentials, means for sensing electrical potentials at selected ones of the sensing electrodes, and means for adjusting the applied potentials to maintain the sensed potentials at selected values.

2. The apparatus of claim 1 wherein the driving and sensing electrodes are arrayed in equal numbers in pairs, in which each sensing electrode is paired with at least one of the driving electrodes, and wherein the adjusting means adjusts the applied potentials to maintain the sensed potential at a selected value at the sensing electrode of each pair.

3. The apparatus of claim 1 wherein the driving and sensing electrodes are fixed in position in equal numbers in pairs, in which each sensing electrode is paired with a single one of the driving electrodes, and wherein the adjusting means adjusts the applied potentials to maintain the sensed potential at a selected value at the sensing electrode of each pair.

4. The apparatus of claim 2 or 3 wherein the providing means includes means for storing the provided potentials and means for restoring the stored potentials periodically to the provided potentials.

5. The apparatus of claim 1 wherein said driving electrodes have a surface area in contact with said buffer solution of about 0.25 $cm^2$.

6. The apparatus of claim 1 wherein the driving and sensing electrodes are arrayed respectively along closed paths.

7. The apparatus of claim 6 wherein the driving and sensing electrodes are arrayed respectively along curved paths.

8. The apparatus of claim 5 wherein the driving and sensing electrodes are arrayed respectively in concentric circles.

9. The apparatus of claim 6 wherein the circle in which the driving electrodes are arrayed is positioned radially outward of the circle in which the sensing electrodes are arrayed.

10. The apparatus of claim 9 wherein each sensing electrode is positioned radially inward of and paired with a single one of the driving electrodes, and wherein the adjusting means adjusts the applied potentials to maintain the sensed potential at a selected value at the sensing electrode of each pair.

11. The apparatus of claim 10 wherein the providing means includes means for storing the provided potentials and means for restoring the stored potentials periodically to the provided potentials.

* * * * *